United States Patent [19]

Zambito

[11] 4,051,857
[45] Oct. 4, 1977

[54] DENTAL FLOSS HOLDER

[76] Inventor: James B. Zambito, 1504 S. Arrawana, Tampa, Fla. 33609

[21] Appl. No.: 717,998

[22] Filed: Aug. 26, 1976

[51] Int. Cl.² .......................................... A61C 15/00
[52] U.S. Cl. ...................................................... 132/91
[58] Field of Search .............................. 132/91, 90, 92

[56] References Cited

U.S. PATENT DOCUMENTS

| 691,581 | 1/1902 | Baumeister | 132/91 |
| 893,345 | 7/1908 | Monson | 132/91 |
| 1,279,026 | 9/1918 | Sievers | 132/92 R |
| 2,172,591 | 9/1939 | Peterson | 132/92 A |

*Primary Examiner*—G.E. McNeill
*Attorney, Agent, or Firm*—Duckworth, Hobby, Orman, Allen & Pettis

[57] ABSTRACT

An improved dental floss holder for simplifying and improving personal dental hygiene. The improvement comprises a cog and tooth structure whereby the strip of dental floss may be angularly oriented by the user to facilitate placement of the floss between each of his tooth pairs. This angular orientation is accomplished by linear movement of a slide member operatively connected to the dental floss holding head.

2 Claims, 7 Drawing Figures

U.S. Patent     Oct. 4, 1977     4,051,857
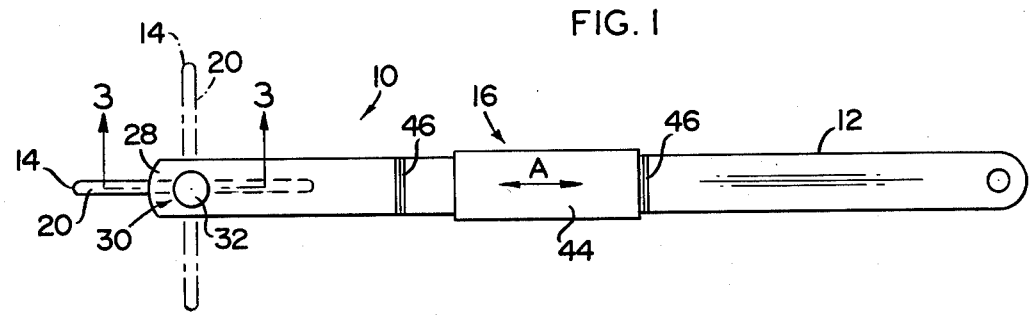
FIG. 1
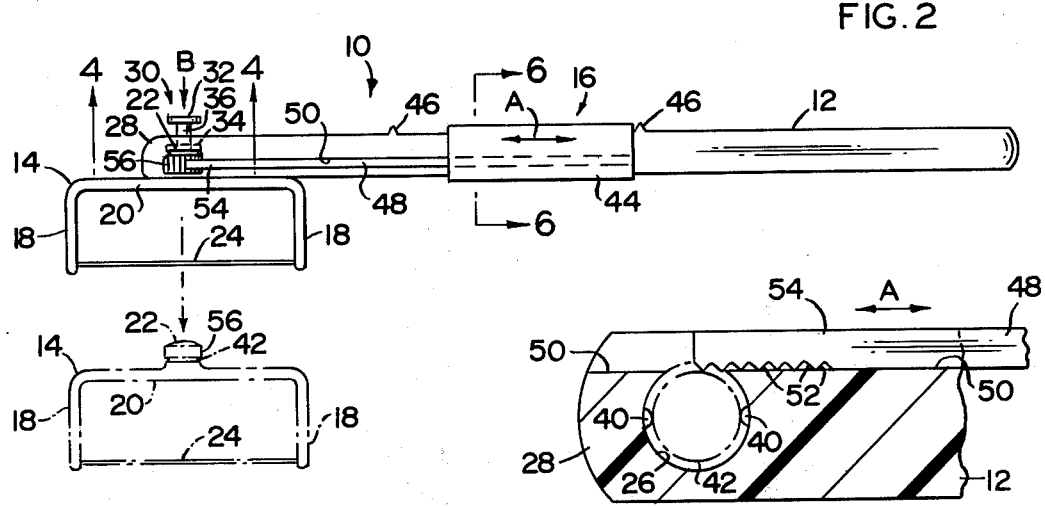
FIG. 2
FIG. 4
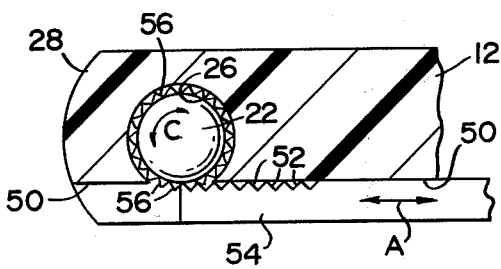
FIG. 5
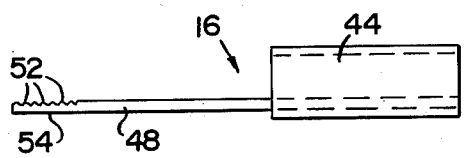
FIG. 7
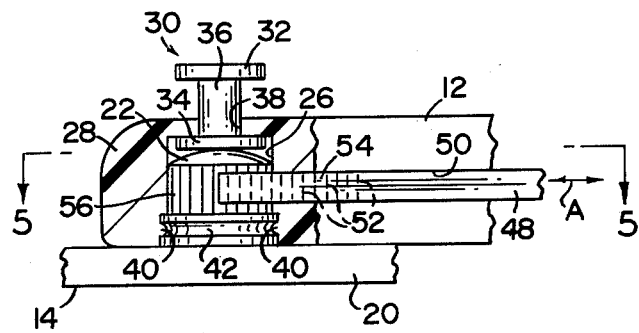
FIG. 3
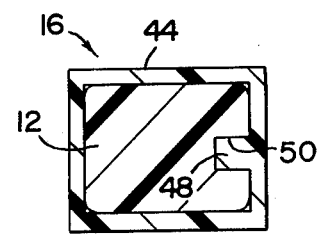
FIG. 6

DENTAL FLOSS HOLDER

BACKGROUND OF THE INVENTION

1. Field of the Invention

The present invention relates to an improved dental floss holder including means whereby the user may reorient the floss holding head for greater ease in performing the flossing operation.

2. Description of the Prior Art

In modern times the science of dentistry has advanced from one of treating and correcting disease and disorder to one of prevention. Of particular importance in the development of preventive dentistry techniques has been the emergence of a dental specialty known as periodontics. Periodontics is that branch of dentistry that deals with diseases of the supporting structures of the teeth. One important aspect of preventive, periodontal dentistry is the prevention and elimination of plaque along the gum line at the base of the teeth.

It is well-known to use a material, generally comprising strands of nylon thread, called floss to remove plaque from between teeth. Till relatively recent times, floss was utilized by wrapping free ends of the material around the user's fingers, and the floss was then successively passed between tooth pairs. Recent developments in the art have resulted in various constructions for floss holders/applicators. These devices normally take the form of a pair of spaced apart legs across which a length of floss material is fixed. A handle device is normally attached to the legs across which the floss is fixed. This device can then be used, somewhat like a toothbrush, for cleaning the interdental spaces.

However, as should be readily apparent, the fixed, spaced apart legs of such devices are neither as flexible nor as movable as are fingers. Accordingly, most users of such devices experience difficulty in placing and manipulating the floss between their teeth, but particularly between their rearmost molars. In an attempt to solve this problem, certain prior art devices have oriented the floss holding legs angularly with regard to the device handle. However, this fixed, angular orientation simply does not provide for easy operation between each possible tooth pair.

Accordingly, it is clear that there is a great need in the art for a floss holding device wherein the floss segment itself can be angularly adjusted with respect to the handle to provide for ease of use and a variety of interdental locations. Inasmuch as the device is primarily intended for hand manipulation, it should be fabricated from a relatively lightweight material. In light of its intended use for dental hygiene purposes, the device must obviously be manufactured from a material which can be easily cleaned. In fact, it would be preferable if the device were manufactured from a sterilizable composition. Both for ease of use and for purposes of sanitation, it would be preferable if that portion of the device holding the length of dental floss could be disposable somewhat like a cartridge-type safety razor.

SUMMARY OF THE INVENTION

The present invention relates to an improved dental floss holder wherein the head utilized to retain a predetermined length of dental floss for use may be selectively oriented by the user for ease of application between different pairs of teeth in the user's mouth. The basic dental floss holder of the invention comprises a toothbrush-like handle, a floss holding head attached to the handle, and connecting means attached to the head and dimensioned and configured to allow a removable connection between the head and the connection means. The improvement of the present invention comprises head positioning means mounted on the handle and operatively engaging the floss holding head, whereby the head and therefore the length of dental floss material may be angularly oriented with respect to the handle.

In the preferred embodiment the floss holding head comprises a pair of spaced apart leg means connected by a base having a connector button formed thereon. A length of dental floss material is fixedly attached across the open ends of the legs, and the connector button removably engages the connecting means formed at one end of the handle. In effect, then, the floss holding head is snap-fitted into the connecting means. The connecting means further includes a plunger means movably mounted therein, whereby depression of the plunger will eject the floss holding head.

The head positioning means of the invention comprises a sleeve means disposed in contiguous, surrounding relationship to a predetermined section of the handle. An arm is integrally formed on the sleeve and extends forwardly therefrom in the direction of the device connecting means. A corresponding track is formed in one side of the handle, and the arm is received within that track. Formed at the forward end of the arm are a plurality of teeth. Correspondingly configured cogs are formed on a predetermined portion of the floss holding head connector button, and these cogs intermesh with the arm's teeth. Finally, stop means are disposed on the handle in spaced apart relationship on opposing ends of the sleeve means. The purpose of the stop means is to limit the forward and after motion of the sleeve along the handle's longitudinal dimension.

In use, once a head is inserted into the connecting means formed on the handle, linear motion of the sleeve means will result in successive intermeshing of the arm's teeth and the connector button's cogs. This intermeshing will necessarily result in a translation of the sleeve's linear movement into axial movement of the head connector button. Inasmuch as the button is fixedly attached to the head, a corrseponding angular reorientation of the head and the dental floss held therein will result. It should be obvious that if relative forward motion of the sleeve would result in a clockwise reorientation of that head, rearward motion of the sleeve would result in corresponding counterclockwise reorientation.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which:

FIG. 1 is a top plan view of the improved dental floss holder.

FIG. 2 is a side elevational view of the dental floss holder, partially in section, and exploded to show the removability of the floss holding head.

FIG. 3 is a sectional view taken along line 3—3 of FIG. 1.

FIG. 4 is a sectional view taken along line 4—4 of FIG. 2.

FIG. 5 is a sectional view taken along line 5—5 of FIG. 3.

FIG. 6 is a sectional view taken along line 6—6 of FIG. 2.

FIG. 7 is a top plan view of the head positioning means. Similar reference characters refer to similar parts throughout the several views of the drawings.

DETAILED DESCRIPTION

The present invention relates to an improved dental floss holder, generally indicated as 10. Holder 10 basically comprises a handle portion 12, a floss holding head 14, means for connecting head 14 to handle 12, and head positioning means generally indicated as 16.

As best seen in the view of FIG. 1, and as will be described in greater detail hereinafter, moving head positioning means 16 forward and aft as indicated by double-headed arrow A will result in angular reorientation of head 14 from the position shown in solid lines in FIG. 1 to that shown in phantom.

As best seen in the view of FIG. 2, floss holding head 14 comprises a pair of spaced apart legs 18 connected by base 20. A connector button 22 is formed at substantially the midpoint of base 20. Finally, a predetermined length of dental floss 24 extends in operative position between the opposite ones of legs 18.

As most clearly seen in FIG. 3, the connecting means of the dental floss holder comprises a receptacle 26 formed in forward end 28 of handle 12 and a plunger means 30 operatively connected thereto. Plunger means 30 comprises a top portion 32 which extends above end 28 and a bottom portion 34 disposed within receptacle 26. Top portion 32 and bottom portion 34 are fixedly interconnected by barrel 36 which passes through aperture 38 formed in forward end 28 and communicating with receptacle 26. As indicated in the exploded view of FIG. 2, depressing plunger means 30 in the direction of arrow B ejects floss holding head 14.

As most clearly seen in the views of FIGS. 3 and 4, floss holding head 14 is releasably held in receptacle 26 by the engagement of gripping means 40 formed in receptacle 26 with corresponding annular groove 42 formed on connector button 22. For purposes of illustration only, gripping means 40 may comprise spring elements or protrusions formed on the inside of receptacle 26. In practice, two such gripping means 40 have been found to provide satisfactory results.

As best seen in FIG. 2, head positioning means 16 comprises a sleeve 44 disposed in contiguous, sliding relationship around a predetermined segment of handle 12. Stop means in the form of ridges 46 are formed in spaced apart relation on handle 12 and serve to limit the forward and aft motion of sleeve 44. As best seen in the sectional view of FIG. 6, an arm 48 is integrally formed on sleeve 44 and extends toward forward end 28 of handle 12. A track 50 is formed along the side of handle 12, and track 50 is dimensioned and configured to receive arm 48 therein as sleeve 44 is moved forward and aft as indicated by arrows A. As shown in FIGS. 4 and 5, track 50 intersects receptacle 26 to define a chord across the aperture defined by receptacle 26.

A plurality of teeth 52 are formed on forward end 54 of arm 48 in communicating relationship to the interior of receptacle 26. A plurality of correspondingly configured cogs 56 are formed around the perimeter of connector button 22 so as to operatively engage teeth 52 when floss holding head 14 is inserted into connecting means receptacle 26 formed on forward end 28 of handle 12. By virtue of this operative engagement between teeth 52 and cogs 56, when sleeve 44 is moved forwardly, toward head 14, connector button 22 and therefore head 14 will rotate clockwise, as indicated by double-headed arrow C. Similarly, after movement of sleeve 44 will result in counterclockwise reorientation of floss holding head 14.

It is by virtue of the construction set forth above that manipulation of sleeve 44 will result in angular reorientation of floss holding head 14 through an angle of least 90° with respect to the longitudinal dimension of handle 12, as shown in phantom.

It will thus be seen that the objects set forth above, among those made apparent from the preceding description, are efficiently attained, and since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. In a dental floss holder comprising a handle, a floss holding head attached to said handle, and connecting means attached to said handle, both said head and said connecting means being dimensioned and configured to be detachably connected to one another, the improvement comprising head positioning means mounted on said handle in movable, engaging relationship to said floss holding head, said head positioning means comprising sleeve means disposed in contiguous, sliding relationship around a predetermined segment of the outer surface of said handle; arm means formed on said sleeve means and extending forwardly therefrom in substantially parallel relationship to the longitudinal dimension of said handle; track means dimensioned and configured to receive said arm means therein formed on said handle; and a plurality of stop means formed on said handle in motion-limiting relation to said sleeve means; said arm means further comprising a plurality of teeth means formed on the forward end thereof in operative relation to a predetermined portion of said head, said head including a plurality of cog means formed on said predetermined portion, whereby longitudinal sliding of said sleeve means results in corresponding intermeshing of said teeth means and said cog means to angularly orient said head with respect to the longitudinal dimension of said handle.

2. An improved dental floss holder as in claim 1 wherein said track means intersects said connecting means, said connecting means comprising a substantially circular aperture formed in said handle, whereby a portion of said track means defines a chord across said aperture.

* * * * *